(12) United States Patent
Whitehead et al.

(10) Patent No.: US 9,134,264 B2
(45) Date of Patent: Sep. 15, 2015

(54) MONITORING METHOD

(75) Inventors: Paul Whitehead, Oxon (GB); John Andrew Walker, Berks (GB)

(73) Assignee: VWS (UK) Limited, Marlow, Buckinghamshire (GB)

( * ) Notice: Subject to any disclaimer, the term of this patent is extended or adjusted under 35 U.S.C. 154(b) by 299 days.

(21) Appl. No.: 13/995,865

(22) PCT Filed: Jan. 11, 2012

(86) PCT No.: PCT/GB2012/050045
§ 371 (c)(1),
(2), (4) Date: Aug. 29, 2013

(87) PCT Pub. No.: WO2012/101419
PCT Pub. Date: Aug. 2, 2012

(65) Prior Publication Data
US 2013/0328579 A1 Dec. 12, 2013

(30) Foreign Application Priority Data
Jan. 26, 2011 (GB) .................................. 1101329.9

(51) Int. Cl.
*G01N 27/06* (2006.01)
*C02F 1/00* (2006.01)
(Continued)

(52) U.S. Cl.
CPC ............... *G01N 27/06* (2013.01); *B01J 47/024* (2013.01); *B01J 47/14* (2013.01); *C02F 1/008* (2013.01);
(Continued)

(58) Field of Classification Search
CPC ....... G01N 27/06; G01N 27/10; B01J 47/024; B01J 47/14; C02F 1/008; C02F 1/42; C02F 2103/04; C02F 2209/006; C02F 2209/05
USPC .................. 324/693, 691, 649, 600, 439, 722
See application file for complete search history.

(56) References Cited

U.S. PATENT DOCUMENTS 5,518,608 A 5/1996 Chubachi
7,357,871 B2 * 4/2008 Nagata et al. ................. 210/662
(Continued)

FOREIGN PATENT DOCUMENTS

DE 19841568 A1 5/1999
EP 0190739 A2 8/1986
(Continued)

OTHER PUBLICATIONS

"Purelab Ultra Brochure", Elga Labwater, Apr. 23, 2012, 2 pages.
(Continued)

*Primary Examiner* — Hoai-An D Nguyen
(74) *Attorney, Agent, or Firm* — Drinker Biddle & Reath LLP

(57) ABSTRACT

A method for monitoring the effectiveness of an ion exchange module in an ultrapure water purification circuit containing ultrapurified water and having a purified water inlet and a point of use outlet and a memory, the method including the steps of measuring the resistivity of ultrapurified water using one or more sensors to provide an ultrapurified benchmark resistivity value $R_i$; introducing purified water into the circuit and passing the water through the ion exchange module; measuring the resistivity of the water to provide a new water resistivity value $R_{new}$; and comparing $R_i$ and $R_{new}$ to determine the effectiveness of the ion exchange module.

22 Claims, 7 Drawing Sheets

(51) Int. Cl.
*C02F 1/42* (2006.01)
*G01N 27/10* (2006.01)
*B01J 47/02* (2006.01)
*B01J 47/14* (2006.01)
*C02F 103/04* (2006.01)

(52) U.S. Cl.
CPC ...... *C02F 1/42* (2013.01); *G01N 27/10* (2013.01); *C02F 2103/04* (2013.01); *C02F 2209/006* (2013.01); *C02F 2209/05* (2013.01)

(56) References Cited

U.S. PATENT DOCUMENTS

2002/0168773 A1* 11/2002 Ito et al. .................. 436/37
2008/0245737 A1 10/2008 Coulter
2013/0320987 A1* 12/2013 Passot et al. .................. 324/425

FOREIGN PATENT DOCUMENTS

| | | |
|---|---|---|
| EP | 1465273 B1 | 9/2009 |
| JP | 11101761 | 4/1999 |
| JP | 20077216173 | 8/2007 |
| WO | 2010043896 A1 | 4/2010 |

OTHER PUBLICATIONS

UK Search Report, GB1200402.4, Apr. 26, 2012, 2 pages.
International Preliminary Report on Patentability, WIPO, PCT/GB2012/050045, Aug. 8, 2013, 5 pages.

* cited by examiner

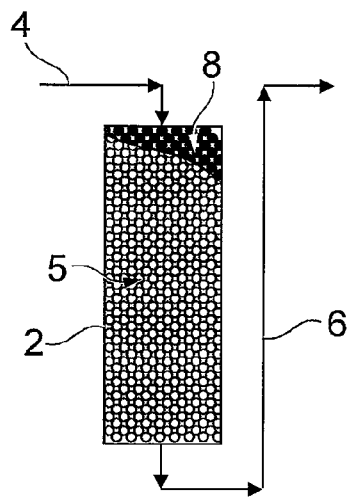
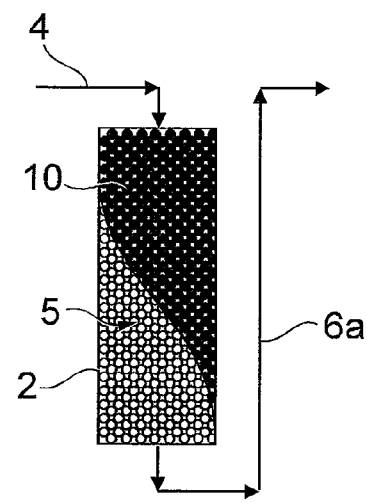
Fig. 2a  Fig. 2b
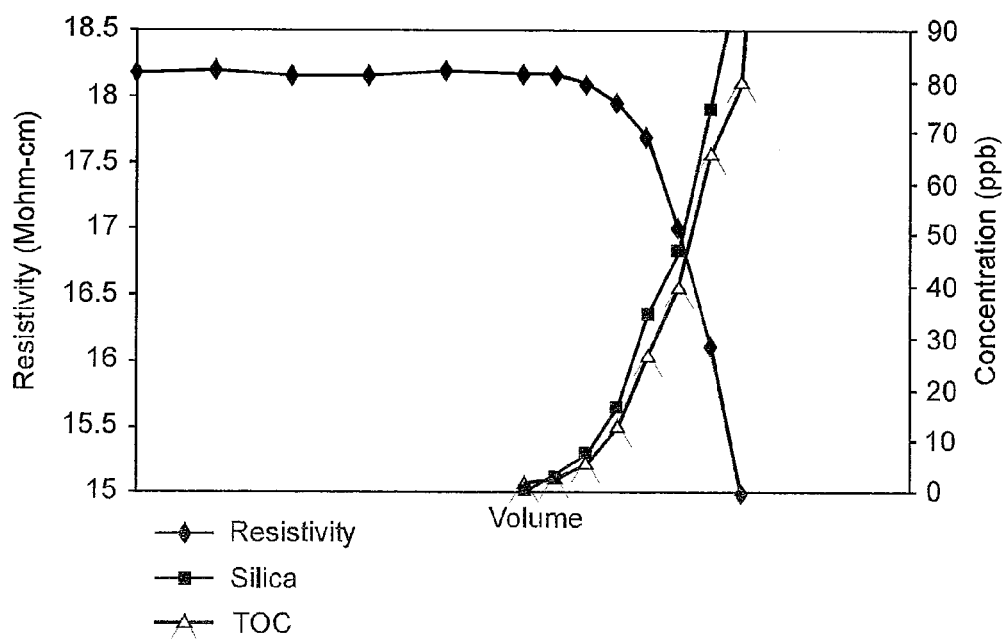
Fig. 3

MONITORING METHOD

FIELD OF HE INVENTION

The present invention relates a method of monitoring the effectiveness of an ion exchange module, such as an ion exchange cartridge pack, in an ultrapure water purification circuit, particularly but not exclusively for use in laboratories.

BACKGROUND

Water purification apparatus and units for use in laboratories and healthcare facilities are well known. Generally, they involve the reduction and/or removal of contaminants and impurities to very low levels. They contain a variety of technologies that remove particles, colloids, bacteria, ionic species and organic substances.

Some uses or applications for water require the water to be not just purified, but 'ultrapurified', i.e. to have a particularly low content of ionic impurities, typically with individual ion concentrations at less than 1 ug/l (1 part per billion or 1 ppb), and often at less than 10 ng/l (10 parts per trillion or 10 ppt). Such applications include the use of the water in the preparation of samples and standards for ultra-trace analytical techniques such as inductively-coupled plasma mass spectrometry (ICP-MS). SEMI standard F63-0309 specifies a maximum contamination of metals of 0.02-0.1 ppb (20-100 ppt) for each element for ultrapure water used in semi-conductor processing.

To achieve ionic purity approaching that of 'absolute' pure water, water purification equipment and systems include one or more dedicated final ion exchangers (IX), usually but not limited to containing one or more resins, typically a mixture of anion and cation resins. These resins contain a large number of active sites on which the "impurity ions" in the purified 'feed' water are taken up. In so doing, they replace hydrogen and hydroxyl ions which recombine to form water. These ion exchangers, (typically in the form of one or two cartridge packs), are usually included in a 'water polisher'—a point-of-use system having a circuit fed with purified water.

If designed correctly, the water polisher functions as a very effective scavenger of residual impurity ions. However, as the capacity (i.e. number of free active sites) of the resin becomes used up (exhausted), those species that have built-up on the resin start to be released into the now 'ultrapure' product water. Because the impurity ions have been concentrated on the resin or resins (hereinafter "resin") they can be eluted into the final ultrapure product water at far higher concentrations than in the water prior to polishing.

It is, therefore, of critical importance to change the pack containing the ion-exchange resin before significant release of ions into the product water occurs.

The established method for detecting the exhaustion of the ion-exchange resin is by monitoring the electrical resistivity of the purified water. Very pure water that is totally free of contaminant ions is often quoted as having an electrical resistivity (referred to as "resistivity") of '18.15' MΩ·cm at 25° C. (due to the slight dissociation of water molecules into hydrogen and hydroxyl ions). This figure is often rounded up to a more general figure of '18.2' MΩ·cm at 25° C.

All resistivity measurements mentioned hereinafter are defined at the 'standard' temperature of 25° C. used for such measurements, and which is not therefore listed each time.

Sufficient quantities of undesired ions present in the water reduce its resistivity, and when a pre-determined drop in resistivity is detected, the cartridge pack is replaced with one containing unused resin.

This way of detecting the need to change the pack has the advantage of simplicity and low cost, but is not adequately sensitive to prevent the release of some ions, and in particular ions which are weakly held to the resin, at levels which could interfere with the very high purity applications described above. For example, FIGS. 2a and 2b of the accompanying drawings show an in-line ion exchange cartridge 2 having a resin bed 5 therein and a water stream 4 passing thereinto to provide a post purified water stream 6. When the ion exchange cartridge 2 is new, with only a portion of resin 5 used (shown as portion 8 in FIG. 2a), then FIG. 2a lists a resistivity measurement of '18.2' MΩ·cm, with less than a 0.05 ppb level of sodium and less than a 1 ppb level of silica.

When a significant portion of the resin 5 in the cartridge 2 is used, shown as portion 10 in FIG. 2b, then only a small change in resistivity (to 18.1 MΩ·cm) has nevertheless now revealed significant increases in the presence of ionic species in the post water stream 6a, now being measured at 1 ppb for sodium, and 50 ppb for silica.

FIG. 3 shows a graph of one example of the change in resistivity in a purified water stream as ion exchange resin is used up in an ion exchange pack, and the increased presence of silica and total organic content (TOC)) in the product water.

Furthermore, direct resistivity measurements have the following limitations:

1/ Commercially available on-line resistivity sensors or meters (generally termed 'line cells') are at best only accurate to +/−0.75% i.e. +/−0.14 MΩ·cm at 18.15 MΩ·cm. The change in resistivity for a typical salt such as sodium nitrate is about 0.5 MΩ·cm for 1 ppb at 18 MΩ·cm. Therefore, even the best resistivity monitoring can only detect +/−0.28 ppb. Lower concentrations currently go undetected.

2/ Line cell measurements are also very sensitive to temperature. Whilst line cells usually have in-built correction for temperature, changes in water temperature are usually slower to show than changes in electrical resistivity (due to thermal lag), which lead to inaccuracies of readings. Electrical interference can also occur in measuring systems, such as during valve switching. Such occurrences may not affect less sensitive resistivity analyses, or analyses allowed to have more time, but they do affect ultrapure water measurements, and so mask changes in the ultrapurification that may not be detected until too late.

3/ Some species, such as those containing silicon and boron, are only slightly ionized and therefore produce much smaller contributions to the resistivity, but nevertheless contaminate the ultrapure water.

4/ The residual resistivity of pure water, nominally at '18.15' MΩ·cm, is due to the very slight dissociation of water molecules into hydrogen and hydroxyl ions. However, the presence of sub-ppb levels of metal ions as shown in Table 1, and as shown graphically in the accompanying FIG. 4, actually decreases the concentration of free hydrogen ions resulting in a rise in resistivity, effectively masking the presence of the impurity ions. Thus, and as shown in Table 1, a resistivity measurement of 18.04 MΩ·cm, which is conventionally regarded as still 'satisfactory' for the ion exchange resin, masks higher levels of certain metal ions in the believed 'ultrapure' water, which is not desired.

TABLE 1

| Metal | Possible Concentration (ppb) at a Resistivity (MΩ.cm) of: | | | | |
| --- | --- | --- | --- | --- | --- |
| | 18.15 | 18.04 | 17.80 | 17.40 | 16.40 |
| Sodium | 0.9 | 1.2 | 1.5 | 1.9 | 2.8 |
| Magnesium | 0.4 | 0.6 | 0.8 | 1.0 | 1.4 |
| Potassium | 0.4 | 1.1 | 1.7 | 2.4 | 3.8 |
| Calcium | 0.5 | 0.8 | 1.1 | 1.5 | 2.2 |
| Chromium | 0.3 | 0.6 | 0.8 | 1.2 | 1.8 |
| Iron | 1.1 | 1.3 | 1.7 | 2.2 | 3.2 |
| Nickel | 1.1 | 1.4 | 1.8 | 2.3 | 3.4 |
| Lead | 1.4 | 3.4 | 4.6 | 6.6 | 10.3 |

Users of water ultrapurification units need to know the water quality and it is usually displayed in 'real time' as the user is operating the unit. When the quality is of a lower resistivity than a pre-determined level, an alarm is often raised. However, as there can be many possible variations in the resistivity readings, as discussed above, the alarm point is usually set significantly below 18.2 MΩ·cm, typically at 10, 15, 16 or 17 MΩ·cm. As discussed above, an alarm point set at 15 MΩ·cm can already have significant levels of contaminants therein at the ppb and ppt levels, being unacceptable to very high quality users.

Moreover, any short term transient drops in the resistivity of ultrapure water are often smoothed over time, (and often occurring at a time when the user is not actually present with the unit to notice) resulting in a seemingly long-term acceptable resistivity level, whilst in the short term being unacceptable.

These factors make the simple 'real-time' monitoring of product water resistivity ineffective as a means of preventing the release of sub-ppb concentrations of trace impurities.

To change the pack in a timely fashion—before impurity ions are released—there are two current approaches in use:

1/ The ion-exchange capacity of the resin-containing pack is known; the water usage is logged and its effect on resin capacity calculated. The pack can then be changed well before the pack's ion-exchange capacity approaches exhaustion. This can be facilitated by feeding the pack with quite high-purity water and/or using large packs to ensure long life for the cartridge pack. However, large packs are undesirable, and this approach can waste substantial amounts of ion-exchange capacity. It is also subject to the normal risks associated with human error.

2/ In multistage monitoring, two ion exchange purification cartridge packs are arranged in series with an additional resistivity cell installed between the two cartridges. When exhaustion of the first stage purification pack is detected by an additional resistivity cell (required to be installed between the two cartridges), the pack is replaced with the second stage polishing pack—which is virtually unused (typically less than 2% when the intermediate resistivity reaches 1 MΩ·cm)—and a new pack fitted in the second, critical stage. This is a highly effective approach but is relatively complex with multiple packs and monitoring.

SUMMARY OF THE INVENTION

It is an object of the present invention to provide a means of detecting when ion-exchange resins are approaching exhaustion and need to be replaced, which does not require the presence of two packs and extra monitoring equipment, nor waste resin capacity and rely on usage estimates.

In one aspect of the present invention, there is provided a method for monitoring the effectiveness of an ion exchange module in an ultrapure water purification circuit containing ultrapurified water and having a purified water inlet and a point of use outlet and a memory, the method comprising the steps of:

(a) passing the water in the circuit through the ion exchange module a multiple of times to provide ultrapurified water;

(b) measuring the resistivity of the ultrapurified water provided by step (a) using one or more sensors to provide an ultrapurified benchmark resistivity value $R_1$;

(c) storing the value $R_1$ in the memory;

(d) introducing purified water into the circuit through the inlet;

(e) passing the water in the circuit including the purified water of step (d) through the ion exchange module;

(f) measuring the resistivity of the water after step (e) to provide a new water resistivity value $R_{new}$; and (g) comparing $R_1$ and $R_{new}$ to determine the effectiveness of the ion exchange module.

In this way, comparing the impact on the resistivity of newly introduced purified water after its first passage through the ion exchange module with the benchmark resistivity value $R_1$ provides a better indicator of the effectiveness of the ion exchange module.

The ion exchange module may have any size, shape and design, and may comprise and/or may be provided in one or more sections, portions, packs or cartridges. Generally, the ion exchange module includes one or more resins, usually in the form of 'beds' of resins, such resins known to be one or more of the group comprising: anionic, cationic, non-ionic, and mixtures thereof; optionally in one or more differing layers along the path of the ion exchange module.

Whilst the present invention may involve two or more distinct ion exchange units or areas or 'beds' of resin as the ion exchange module, the ion exchange module is preferably provided as, with or in, a single ion exchange pack or cartridge, and in a relatively low volume.

The ion exchange module is not limited to comprising the same composition and/or component(s) during the measurement of $R_1$ and $R_{new}$.

There are a number of benefits, both technical and practical, to using relatively low volume ion exchange resin beds as the ion exchange module. For example, the media is more efficient when used for a shorter period of time. As the volume of resin that is exhausted increases the extent of media blinding/degradation and scope for bacterial growth also increases. For these and other reasons the Clinical Laboratory Standards Institute (CLSI) recommends that "resin bed volumes should be kept as small as reasonably possible".

A consequence of using a relatively small ion-exchange resin bed in a system that recirculates water from a reservoir is the possibility of better predicting/detecting incipient pack exhaustion. This can be used to pre-empt the release of ionic species such as silica.

The kinetics of the ion-exchange process are such that as the resin becomes exhausted the water requires multiple passes through the resin bed before all ions are removed. This can be observed during the initial portion of the purification cycle in a temporary drop in resistivity in the water after the ion-exchange bed. The depth and duration of this drop in resistivity increase as the resins are used. The extent of this transient change can be monitored and related to the release of ions from the pack. A suitable alarm point can be set to avoid the release of ions at a level of significance to the application of the water.

The ultrapure water purification circuit is preferably part of a 'water polisher' as described herein, and/or part of, either separately but preferably integrally, a water purification apparatus providing the purified water. Thus, the purified water provided for step (a) is created by the reduction and/or removal of any or one or more of the contaminants and impurities in a feed water stream. This can involve the reduction and/or removal of one or more of the following: particles, colloids, bacteria, micro-organisms, ionic species, organic substances.

A feed water stream to a water purification apparatus may comprise any source of water, generally being a potable water source, generally available to a user from a mains supply or other continuous or large supply or source. Commonly, such a water source is provided from a tap or other standard supply device, having a line or other connection with the water purification apparatus.

The water purification apparatus may comprise any number of devices, parts, components, lines, etc, including but not limited to one or more of the following: pumps, meters, sensors, oxidisers, de-ionisers, valves, drains, control units and mechanisms, taps, filters, membranes.

In general, a water purification apparatus or unit able to provide purified water for the present invention at least comprises: a water inlet, a pump, a de-ioniser, and a water outlet (for dispense of the purified water). Many types and forms of de-ionisers are known in the art, and include, but are not limited to, one or more of the following; (electro)deionisation apparatus or units, reverse osmosis (RO) units or apparatus, ion-exchangers, resins and zeolites. The action and operation of a de-ioniser is well known in the art, and they are not further described in detail herein.

Such water purification apparatus are generally 'stand alone' units, generally only requiring connection to nearby water and electricity supplies to be operable. Thus, they are generally independent and/or movable units operating in or at a specific location such as a laboratory. Preferably, at least the majority of the purification actions or processes occur within a housing. They are intended to provide a purified water stream only, such stream not being in combination with any other substance or compound.

In general, such water purification apparatus and units are intended to provide a purified water stream having a conductivity of less than 30 µS/cm. This can be equated to a purified water stream having a resistivity of at least 0.03 MΩ·cm. Additionally, purity specifications can be made for organic species to content levels of less than 500 ppb of total organic carbon (TOC), preferably less than 50 ppb; bacteria to levels less than 100 colony forming units (cfu) per milliliter, preferably less than 1 cfu/ml; and for dissolved oxygen and/or particles.

The skilled man is aware of the relationship between conductivity and resistivity, such that either one or both measurements can be made by a suitable measuring apparatus or device. The skilled man is also aware that conductivity and/or resistivity measurements or values are temperature dependent. As mentioned above, commonly a temperature of 25° C. is used as a standard temperature when discussing and comparing conductivity and/or resistivity measurements.

Apparatus and devices for measuring a resistivity or conductivity value of a water stream are known in the art, generally being sensors or meters, and typically being in-line resistivity 'cells' as discussed hereinabove.

The ultrapure water purification circuit has a purified water inlet, a point of use outlet, and a memory. The purification circuit may include more than one water inlet, and more than one outlet, and one or more further features including but not limited to: pump, reservoir, ion exchange module.

The dispense of at least a portion of the ultrapure water stream can be provided through any form or type of outlet or outlets, optionally being co-ordinated or separate.

The ultrapure water purification circuit may have a dispense mode or other such form of operation, and a recirculation mode. Preferably, the point of dispense involves at least one valve, more preferably operable between a dispense position and a recirculating position. One or more valves may also provide control over the volume and/or rate of flow of the ultrapure water stream at the point of dispense.

The movement of water through or around a water purification circuit is generally provided by the use of one of more pumps known in the art, and not further discussed in detail herein.

Stopping of the dispense of the ultrapure water stream may be carried out by the operation (usually through a controller) of one or more parts or components of the water purification circuit, generally operation of one or more valves at or near the dispense, such as a 2-way valve able to move between a dispense position and a recirculating position.

The intention of the ultrapure water purification circuit is to provide an ultrapure water stream. The term "ultrapure water" as used herein refers to a water stream having a resistivity of at least 18.0 MΩ·cm, preferably at or above 18.1 MΩ·cm, and generally referred in the art as a resistivity of "18.2 MΩ·cm" to the nearest decimal point. The skilled man is aware there is an 'absolute' measurement of pure water, but that on-line resistivity meters are at best only accurate to +/−0.14 MΩ·cm, and are very temperature dependant at such measurement levels. Moreover, temperature lags and electrical spikes also cause variations in the outputs of electrical components such as in-line resistivity calls, as discussed above, especially at the level of accuracy and real-time sensitivity desired by users of the highest purity water at the time of dispense.

Thus, it is the purpose of the present invention to provide a 'benchmark' resistivity value for ultrapure water created by passing water in the ultrapure water purification circuit through the ion exchange module a multiple of times. This benchmark resistivity value is labelled "$R_1$", and can be stored by any suitable storer, generally part of the comparator for the forthcoming comparisons. It provides a benchmark value based on the components carrying out the measurements in the circuit as a way of compensating for possible variations in resistivity measurements at this level of purity measurement.

The ultrapurified benchmark resistivity value $R_1$ can be determined at any time prior to the introduction of new purified water into the circuit through the inlet. In some uses, this may occur immediately prior to the introduction of the purified water, as the ultrapure water purification circuit is in relatively constant demand or use by one or more users. Under other circumstances or in other situations, such as during periods of less demand for ultrapure water, this may result in a time period between uses of the ultrapure water purification circuit, such that determination of the ultrapurified benchmark resistivity value $R_1$ may occur less than immediately prior to the introduction of purified water, such that the value $R_1$ can be stored in a memory.

Generally, the introduction of purified water into the circuit through the inlet occurs after the outflow of at least a portion of the ultrapurified water in the circuit through the point of use outlet, being a single outlet or indeed more than one outlet.

The ultrapure water purification circuit may hold a sufficient volume of water to allow one or more portions of ultra-purified water to be dispensed from a point of use outlet, prior to the need to introduce more purified water into the circuit. In particular, the purification circuit may include a reservoir, that allows the provision of a greater volume of purified water from the purification circuit prior to the need for the introduction of further purified water to 'top up' the purification circuit.

The present invention is preferably adapted for use with a purification circuit having a relatively low volume, in particular a volume of less than 20 liters, such as less than 15 liters or less than 10 liters, which includes the volume of any reservoir.

The introduction of purified water into the circuit may be controlled by the use of one or more valves at or near the inlet. Where the purification circuit already includes some ultrapurified water between the inlet and the ion exchange module, the newly introduced purified water is generally mixed therewith to provide water in the circuit for passage through the ion exchange module. Thus, the water now passing through the ion exchange module may be wholly or substantially purified water, but may also comprise some water still in the circuit, i.e. a proportion of purified water newly introduced into the circuit, and a proportion of already ultrapurified water, which is now less purified following its mixing with the purified water.

After passage of such water in the circuit through the ion exchange module, the resistivity of such water is measured to provide a new water resistivity value $R_{new}$. A comparison can then be made of $R_1$ and $R_{new}$ to determine the effectiveness of the ion exchange module. Optionally, $R_{new}$ is also stored in a memory.

The comparison in step (g) may include a time element.

$R_{new}$ may represent more than one value and may be determined by any suitable algorithm such as a time average. $R_{new}$ may represent a mean, median or other average value over a defined time period. This may at least in part eliminate or smooth erratic values from electrical spikes or temperature calibration lags.

The comparison in step (g) may include a quantitative comparison of the resistivity values, in particular a comparison of the quantitative difference between $R_1$ and $R_{new}$.

According to one embodiment of the present invention, the comparison of $R_{new}$ being greater than a predetermined quantitative difference from $R_1$ determines non-effectiveness of the ion exchange module.

For example, a comparison of $R_1$ and $R_{new}$ being >0.2 or >0.3 or >0.4 or >0.5 or >0.6 or >0.7 MΩ·cm could determine non-effectiveness of the ion exchange module.

That is, where the extent of the decrease in difference between $R_1$ and $R_{new}$ is more than a pre-determined value such as one of the above numbers, the decrease in resistivity shown by the lower $R_{new}$ value is an indicator to the user of the potential undesired release of ionic species from the resin following the passage of the newly introduced purified water (that is at least a portion of the water now passing through the ion exchange module), which are deemed to be unacceptable, so that the ion exchange module requires replacing, such as a new ion exchange pack being introduced into the ultrapure water purification circuit.

According to a further embodiment of the present invention, the method further comprises the steps of:

(h) passing water in the circuit after step (f) through the ion exchange module one or more further times;

(i) taking one or more resistivity measurements of the water after step (h) to provide one or more further resistivity values $R_{2+}$; and (j) comparing at least one of the $R_{2+}$ values and $R_{new}$ to further determine the effectiveness of the ion exchange module.

In this way, a number of further resistivity values, being $R_2$, $R_3$, $R_4$, etc., being any number of further resistivity measurements taken, can be used to further determine the effectiveness of the ion exchange module by comparison with $R_{new}$.

Thus, the term "$R_{2+}$" as used herein refers to one or any number of further resistivity values.

The further resistivity measurements may be taken periodically, regularly or continuously, such as after a regular time period of a pre-determined number of seconds and/or minutes. By the introduction of a time element into the determination of the measuring for further resistivity values, such further resistivity measurements are able to monitor the resistivity of the water in the purification circuit over time, and provide the comparison in step (j) with a time element.

According to a further embodiment of the present invention, the comparison of step (j) includes a comparison of the quantitative difference between $R_1$ and $R_{2+}$.

Thus, the present invention can provide a method which includes a comparison of the quantitative difference between $R_1$ and one of, some of or all of, further resistivity values as represented by the general term "$R_{2+}$". Where the quantititive difference is noted as being the same as or greater than a pre-determined quantitative difference, such as but not limited to 0.1MΩ·cm, 0.2MΩ·cm, 0.3MΩ·cm, 0.4MΩ·cm etc., this could be an alternative and/or additional determinator of the non-effectiveness of the ion exchange module. That is, the inability of the ion exchange module to achieve a resistivity value $R_{2+}$ that is or which remains below $R_1$, by a pre-determined amount indicates exhaustion of the ion exchange resin in the ion exchange module over time, which again can be a further indicator to the user of the need to replace the ion exchange module.

According to a further embodiment of the present invention, the comparison of step (j) further includes a comparison of the quantitative difference between $R_1$, $R_{new}$ and $R_{2+}$.

Overall, the method of the present invention allows the user to consider a range of possible comparators such as time, quantitative difference, optionally divided into one or more multiple comparisons, of the resistivity of water in the purification circuit, to provide one or more indicators, optionally one or more different types or forms of indicator, of the non-effectiveness of the ion exchange module, or indeed an early warning of the non-effectiveness of the ion exchange module prior to the effectiveness of the ion exchange module going beyond a set or pre-determined limit or value according to the ultrapure level of purity required from the purification circuit.

In particular, the method of the present invention provides a determination of the effect on water exiting the ion exchange module (of a water stream entering the ion exchange module) containing at least a portion of purified water, and having a purity (based on resistivity) usually significantly below the purity of any remaining purified water in the purification circuit, which is therefore able to provide a distinct resistivity value ($R_{new}$) which can be used as a comparator of the expected benchmark resistivity value ($R_1$). By providing further measurements of resistivity of the water in the purification circuit after its passage more than once through the ion exchange module, the present invention provides further ability to determine the effectiveness of the ion exchange module as the ion exchange module to purify the water stream a number of times, and its ability to recover from any significant drop in resistivity following the first passage of purified water therethrough.

As mentioned above, resistivity is the reciprocal of conductivity, which is a measurement of the conductive species, including ionic contaminant such as metal ions but not limited thereto, in the water stream.

Thus, according to another aspect of the present invention, there is provided a method determining the presence of one or more contaminants at a level <1 parts per billion in an ultrapure water stream using a method of monitoring the effectiveness of the ion exchange module as described herein.

In particular, the accuracy of the present invention allows the presence of one or more contaminants at levels below 1 ppb (parts per billion) to be determined, allowing the skilled man now to provide an analysis of the presence of one or more metal ions in an ultrapure water stream at a parts per trillion (ppt) level.

BRIEF DESCRIPTION OF THE DRAWINGS

Embodiments of the present invention will now be described by way of example only, and with reference to the accompanying drawings in which:

FIGS. 2a and 2b are representative examples of an ion exchange cartridge showing change in certain water stream values after use of ion exchange resin therein;

FIG. 3 is a graph of resistivity of the water stream in FIGS. 2a and 2b against concentration of silica and TOC;

DESCRIPTION OF THE PREFERRED EMBODIMENTS

Figure 1:
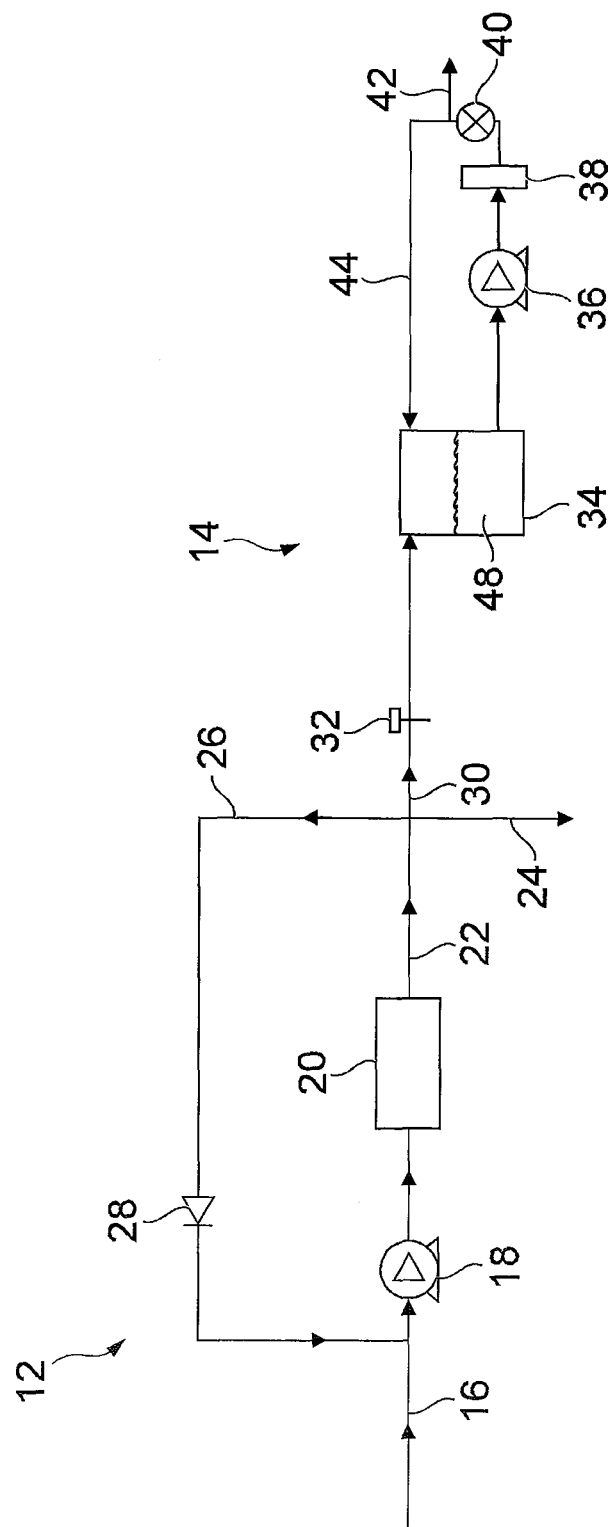
FIG. 1 is a schematic representation of a water purification apparatus including an ultrapure water purification circuit for use in the present invention.

Referring to the drawings, FIG. 1 shows a water purification apparatus 12 and an ultrapure water purification circuit 14. In FIG. 1, there is provided a first feed or supply water stream 16 from a water source (not shown), which may have been pre-treated by one or more steps and/or processes in a manner known in the art, such as one or more filters or membranes or de-ionisers to reduce impurities.

The supply water stream 16 passes through a pump 18 and one or more purification devices, parts, components, etc., generally shown by a schematic box 20. The box 20 could include one or more initial ionic species removal units, such as a reverse osmosis (RO) unit. Optionally, box 20 includes one or more oxidisers or the like generally intended to decompose organic compounds and substances in the supply water stream 6 by oxidising them to form ionic or charge species. Generally, the box 20 provides a purified stream 22 in a manner known in the art.

If desired, the purified water stream 22 can be provided at a suitable purified water point of use outlet 24 for a user, who may only require or desire water purified to the level provided by the water purification apparatus 12.

Alternatively or additionally, the water purification apparatus includes a recirculation circuit 26 having a one-way valve 28 in a manner known in the art, generally to maintain a level of purity of the water in the water purification apparatus 12 during periods of non-supply of the purified water stream 22.

FIG. 1 shows a water stream path 30 to an inlet 32 of the ultrapure water purification circuit 14.

The ultrapure water purification circuit (hereinafter "ultrapure circuit") 14 comprises a reservoir 34, a pump 36, an ion exchange module being a single ion exchange pack 38, an in-line resistivity cell 40, a ultrapure water point of use outlet 42 and a return line 44, as well as lines in between each of the above components to create a complete circuit in a manner known in the art.

Preferably, the ultrapure circuit 14 has a relatively low volume, such as less than 10 liters, with the reservoir comprising the majority volume of for example 7 liters. The nature and operation of the pump 36 and ion exchange module 38, line cell 40 and outlet 42 are known in the art, and may comprise one or more valves thereinbetween in order to allow control by a user or the circuit operator of the actions required of the ultrapure circuit 14. For example, operation for a dispense of ultrapure water from the outlet 42 operates a valve (not shown) to allow ultrapure water to be dispensed from the outlet 42 rather than recirculate via line 44.

As described hereinabove, FIGS. 2a and 2b show drawings of an in-line ion exchange cartridge 2 able to be the ion exchange pack 38 in FIG. 1 and having a resin bed 5 therein. As described above, simple measurement of the resistivity of the post-purified water stream 6, 6a from the ion exchange cartridge 2 may show little change in resistivity (from 18.2 to 18.1 MΩ·cm), but where a significant portion of the resin 5 in a cartridge 2 is used, the only small change in resistivity can mask a significant increase in the presence of ion species in the post-purified water stream 6, 6a due to the differences in resistivity (or conductivity) between hydrogen and hydroxide ions, and the metal ions.

Figure 4:
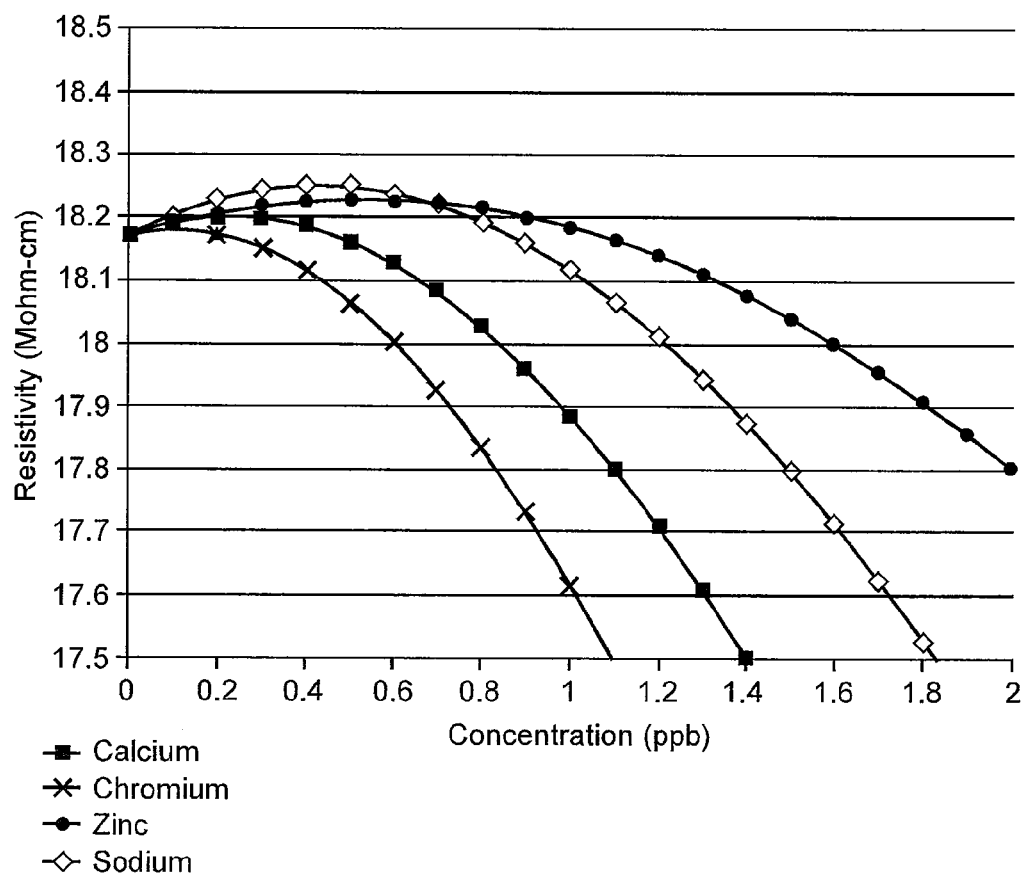
FIG. 4 is a graph of resistivity against concentration of certain metal ions, values for which are listed in Table 1 herein.

The overall rise in the presence of silica and TOC versus resistivity is shown in FIG. 3, and for other metal ions in FIG. 4, with tabulation in table 1 of the concentration of certain metal ions possibly present at five resistivity values.

Figure 5:
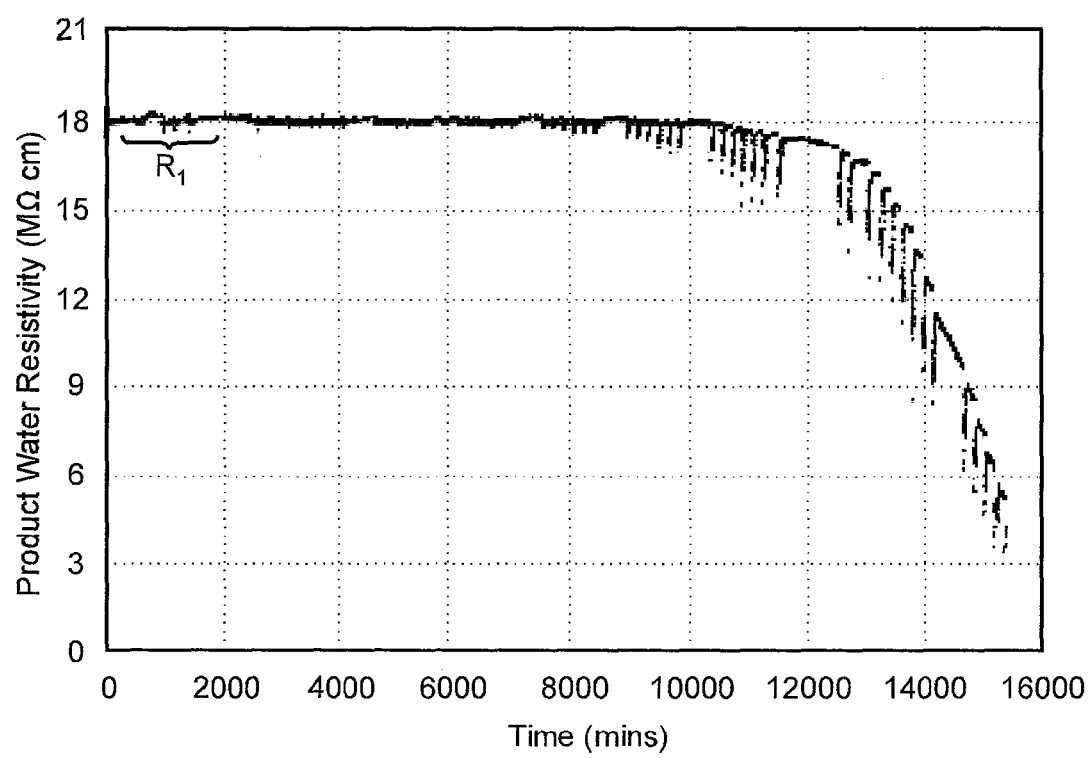
FIG. 5 is a graph of resistivity over extensive time for a purification cycle with resin starting from a new ion exchange pack.

FIG. 5 is a graph of resistivity over an extensive time period, shown as 16,000 minutes, for the overall lifetime of an average ion exchange resin bed in an ultrapure circuit such as that shown in FIG. 1 herewith. The circuit 14 consists of a reservoir with a volume of 7 liters, and a pump which recirculates water typically at 1 liter/minute through an ion-exchange bed with a volume of 300 ml of mixed anion and cation resins. An operational 'cycle' consists of the reservoir being filled with purified water and the water being recirculated through the resin bed to purify it prior to regular dispensing.

At an early stage in the pack life, there is a slight drop in resistivity (to about 18.0 MΩ·cm) before rising again to 18.15 MΩ·cm. As the pack approaches exhaustion, no significant release of ions may have occurred, but there is a much more substantial drop in initial resistivity to about 17.5 MΩ·cm or lower and for a longer period.

The conventional view of when the ion exchange bed is "exhausted", (i.e. starting to release previously captured ionic species back into the water stream, thereby increasing conductivity and reducing resistivity), is based only on the lowest resistivity measured by an in-line resistivity meter. When such a resistivity value reaches for example 5, 10 or 15 MΩ·cm, then the ion exchange resin bed is replaced, usually by the direct replacement of the cartridge containing the resin bed with a new cartridge.

Where the resistivity accuracy is not so critical, that is, a user is happy to accept the possibility of a proportion of ionic species in an 'ultrapure' water product stream, then consideration of the effectiveness of the ion exchange module may not be critical, and conventional consideration of the need to replace an ion exchange module can be used.

However, the present invention is based on an understanding of the effect of the variability and accuracy of measuring components at the purity desired by the present invention. The present invention is based on a comparison of actual resistivity measurements, against any expected or 'standard' resistivity measurements for ultrapure water, which could be (relatively) quite different.

In particular, the present invention is able to consider the effectiveness of an ion exchange module with much greater sensitivity, in order to provide an ultrapure water stream preferably having concentrations of any undesired ionic species, such as metal ions, being below 1 ppb. This is possible by the method of the present invention more precisely being aware of the partial exhaustion of the ion exchange resin in the ion exchange module as now described.

In the present invention, there is a method of monitoring the effectiveness of an ion-exchange module such as the ion exchange pack 38 shown in the ultrapure water purification circuit 14 of FIG. 1. This circuit 14 contains an amount of ultrapurified water, (such as the portion of water 48 shown present in the reservoir 34, and in the circuit lines such as line 44), and has a purified water inlet 32 and a point of use outlet 42 and a memory (not shown).

In a first step, the method comprises passing water in the circuit 14 through the ion exchange module 38 a multiple of times, generally by operation of the pump 36 at a suitable speed, and without withdrawal of any water in the circuit through the point of use outlet 42.

Following this passage of water, the resistivity of the now ultrapurified water (provided or reiterated by the passage of the water in the circuit through the ion exchange module a number of times), and as measurement of an ultrapurified benchmark resistivity value $R_1$ by the in-line cell 40. The value $R_1$ can be stored in the memory of a suitable storer, such as a comparator being part of the operator of the ultrapure circuit 14 and/or the water purification apparatus 12.

Now having a benchmark value $R_1$ the ultrapure circuit 14 introduces a portion of purified water 22 into the ultrapure circuit 14 through the inlet 32. This purified water 22 mixes with ultrapure water already in the ultrapure circuit 14, generally in the reservoir 34 and already having a contamination level of ionic contaminants below 1 ppb. Determination of the timing and volume of purified water 22 to be introduced into the ultrapure circuit 14 is dependent on the user and/or operator of the ultrapure circuit 14 or water purification apparatus 12. Generally, a significant dispense of ultrapure water through the point of use outlet 42, such as more than 50% of the available water in the ultrapure circuit 14, may trigger the operation to provide a 'top up' of water in the ultrapure circuit 14. Alternatively, the reaching of a predetermined volume or level in the reservoir 34 may also be the cause or trigger for the introduction of purified water 22 through the inlet 32.

The ultrapure circuit 14 is now able to pass the purified water 22 newly introduced into the circuit 14, in combination with any ultrapure water already existing in the circuit 14 (for example between the end of the recirculation line 44 and the ion exchange module 38, generally being a portion of ultrapure water 48 in the reservoir 34), through the pump 36 and the ion exchange module 38.

Because the resistivity of the purified water 22 is generally lower, usually significantly lower, than the resistivity of the residual ultrapure water in the circuit 14, the resistivity value of the water in the circuit now passing into the ion exchange module 38 will drop significantly. The water exiting may have an increased concentration of contaminants, and will be measured by the in-line cell 40. Thus, there is a measurement of the resistivity of the water after the above passage of water through the ion exchange module to provide a new water resistivity value $R_{new}$.

The new water resistivity value $R_{new}$ may be a single resistivity value, such as a minimum resistivity value. Alternatively, the new water resistivity value $R_{new}$ maybe an average resistivity value taken over time prior to continuing resistivity measurements achieving a predetermined value.

Figure 6:
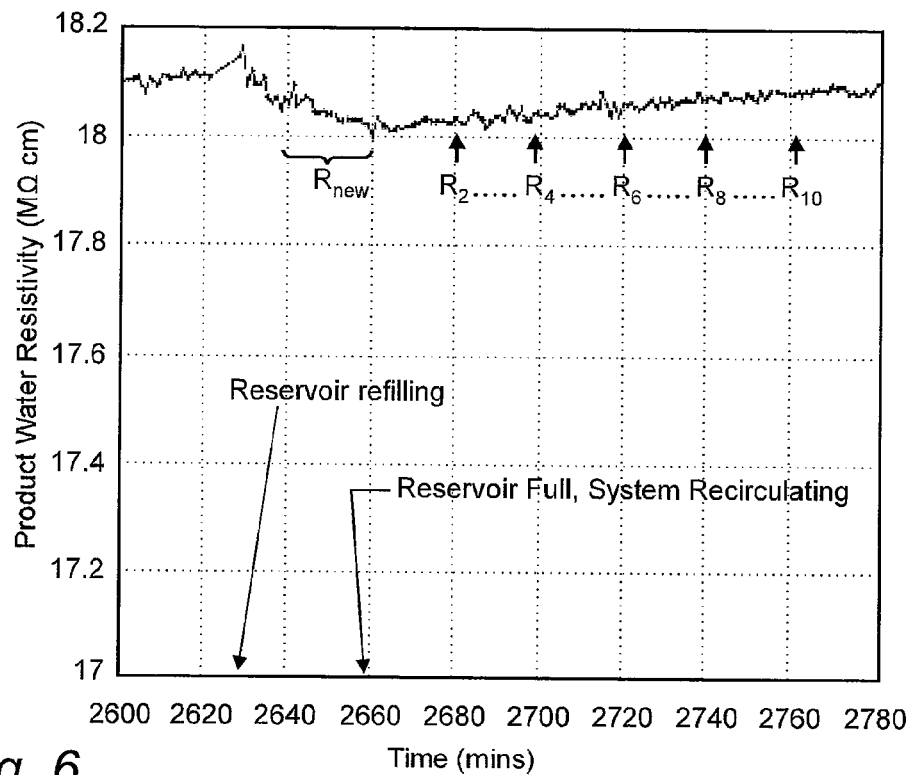
FIGS. 6-11 are five graphs of the same resistivity over five short periods of time taken from within FIG. 5.

FIG. 6 shows a portion of the graph shown in FIG. 5 between the time period 2600 and 2780 minutes. This shows a period of resistivity measurement that is relatively constant some time after refilling of the reservoir 34, and whilst the circuit 14 is in full recirculation.

FIG. 6 shows $R_{new}$ taken as an average valve over measurements made over several minutes shortly after time 2620. This value is approximately 18.15 MΩ·cm.

The present invention is now able to compare $R_1$ and $R_{new}$ to determine the effectiveness of the ion exchange module 38. Whilst there is an expected difference between $R_1$ and $R_{new}$ as shown in FIG. 6, this difference may be considered by the operator or user of the ultrapure circuit 14 to show the continuing effectiveness of the ion exchange module 38, or to be not below a predetermined level of any 'lack' of effectiveness.

Figure 7:
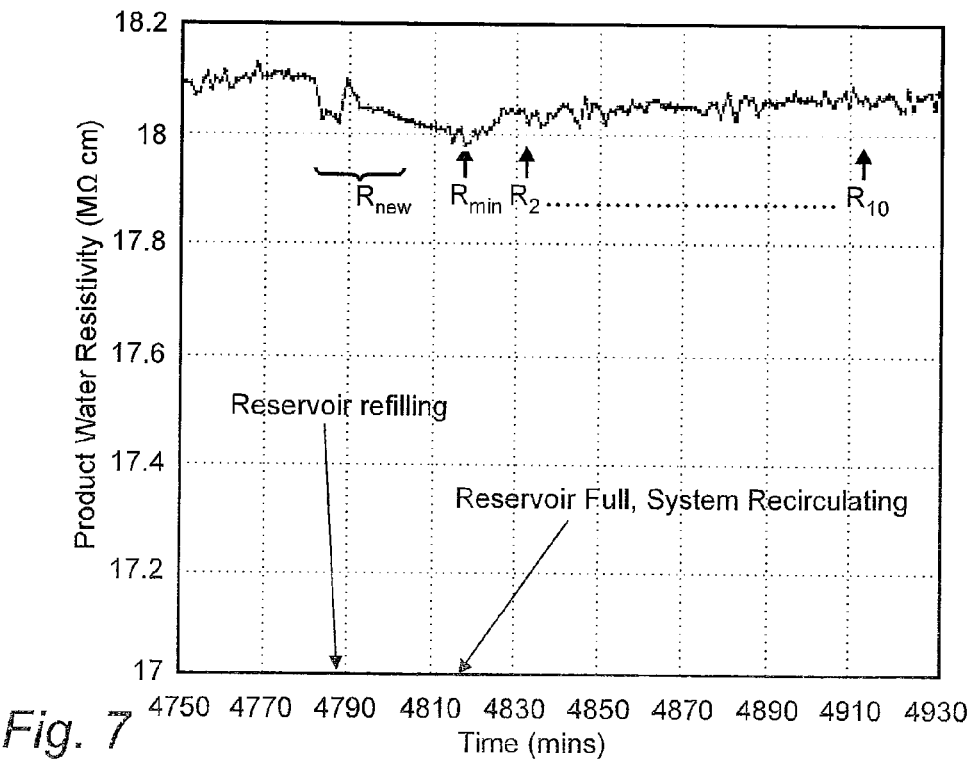
Figure 8:
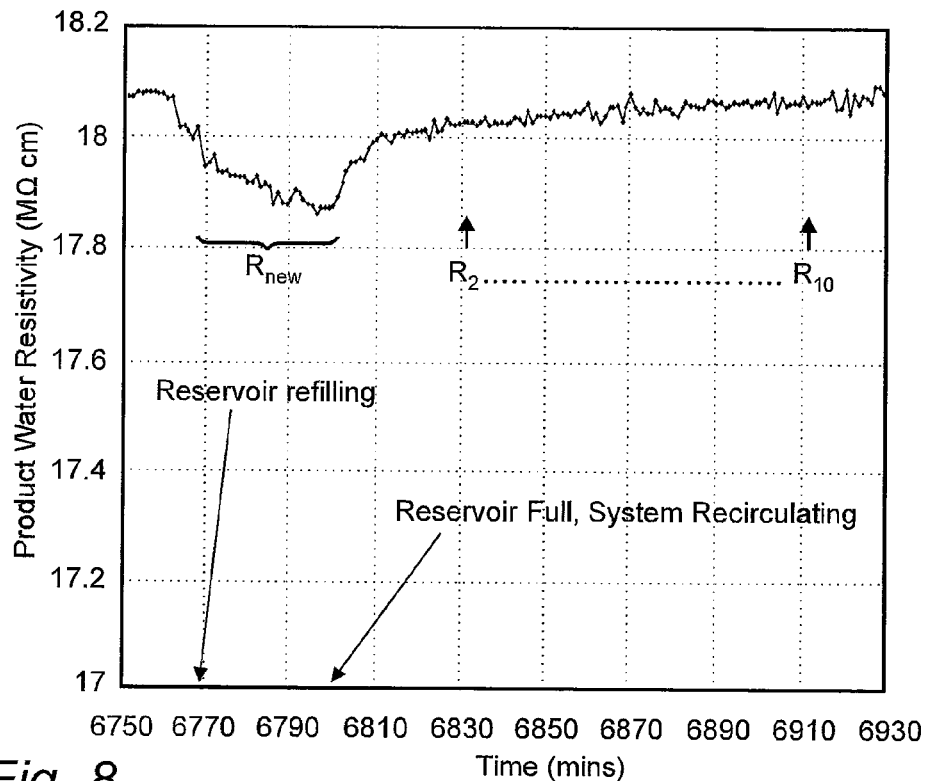

FIGS. 7 and 8 are graphs of resistivity over the time periods 4750-4930 and 6750-6930 minutes respectively of FIG. 5, each showing a different $R_{new}$, which may be taken over the same or a different time period as the $R_{new}$ measurement in FIG. 6, or indeed as described elsewhere. In FIG. 8, $R_{new}$ is now below 18 MΩ·cm for a period of time.

Figure 9:
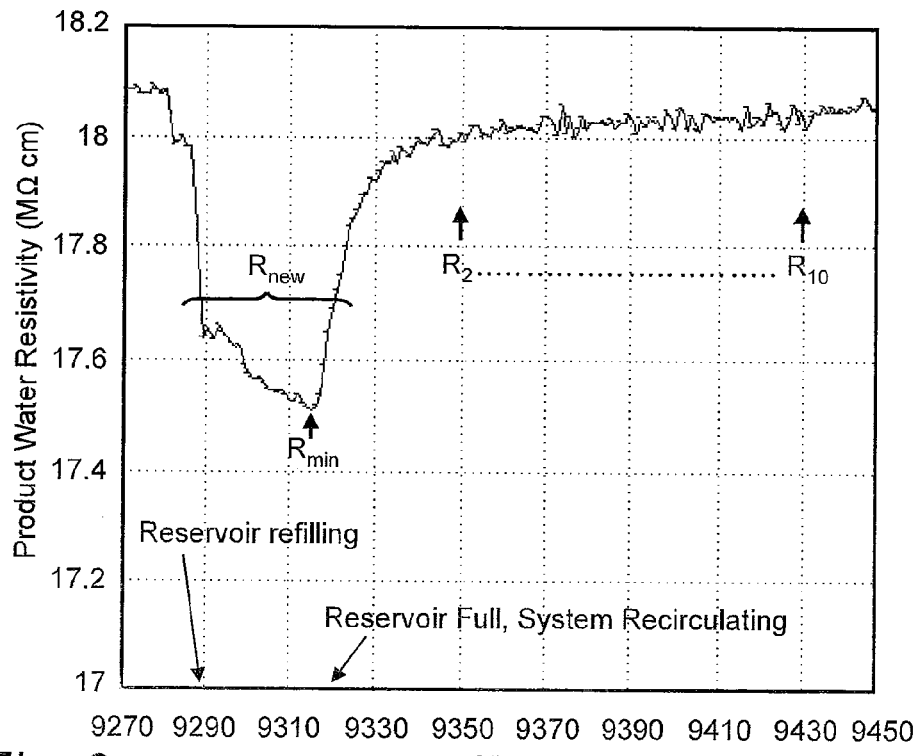

FIG. 9 is a graph of resistivity over the time period 9270-9450 minutes of FIG. 5, showing a different $R_{new}$, either being an $R_{min}$ of about 17.5, or an average of the resistivity value between about 9290 mins and about 9320 mins. Comparison of the $R_{new}$ value selected in FIG. 9 with $R_1$ value can provide another consideration of the effectiveness of the ion exchange module 38.

Figure 10:
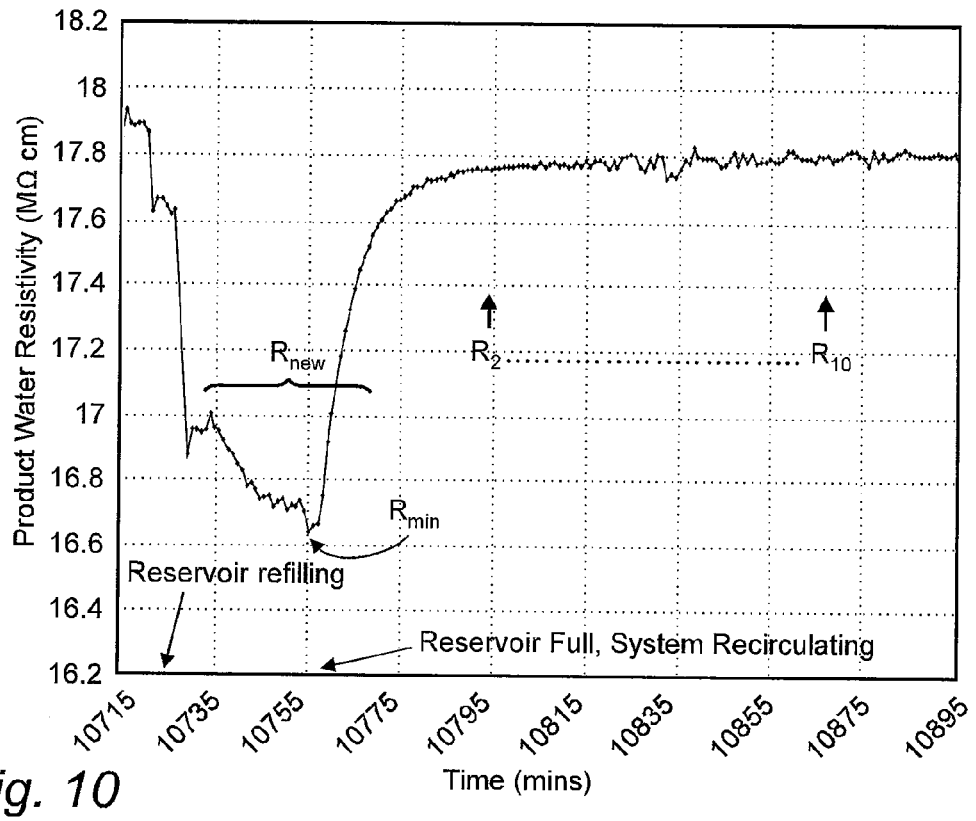
Figure 11:
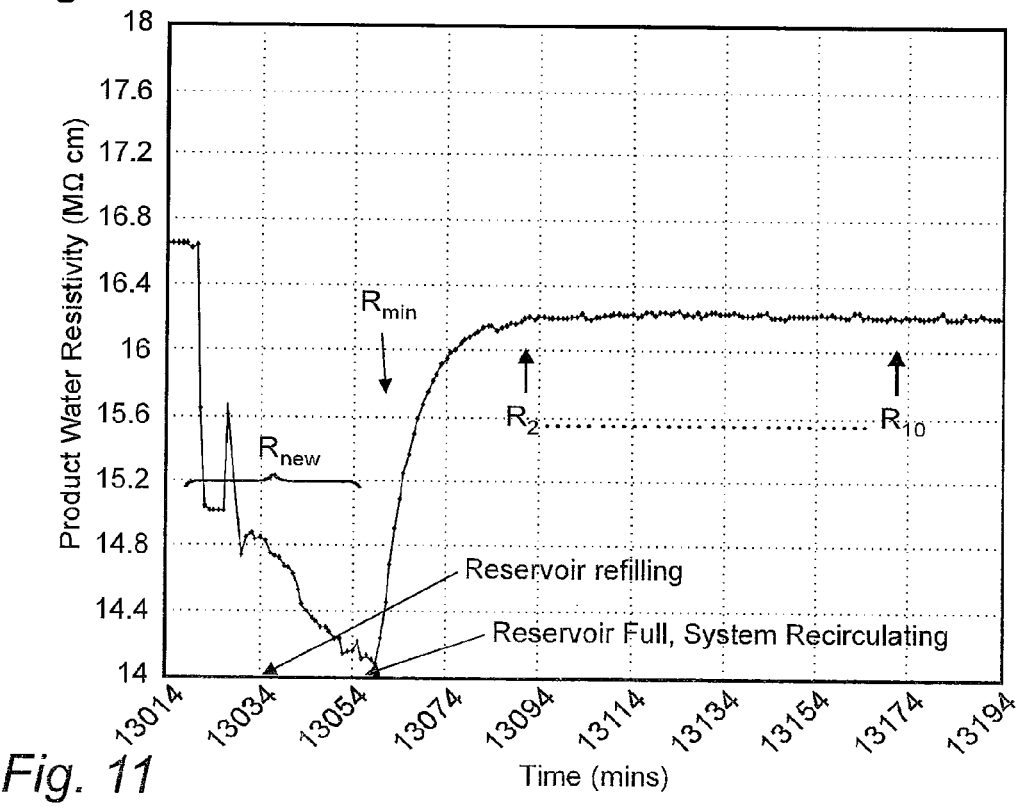

Similarly, FIGS. 10 and 11 show graphs of resistivity over the time periods 10715-10895 and 13014-13194 minutes of FIG. 5, showing still larger differences in resistivity values in the use of the same ion exchange module 38, caused by the introduction of the further portions of purified water 22 into the ultrapure circuit 14. The resin in the ion exchange module 38 is clearly becoming more and more exhausted with ionic species, reducing its effectiveness.

Comparisons of the various $R_{new}$ values that could be taken from FIGS. 6-11 provide the user or operator of the ultrapure circuit 14 with different considerations as to the continuing effectiveness of the ion exchange module 38.

The method of the present invention allows comparison of resistivity values to continue after $R_{new}$. Reference points could be used for time purposes such as relating to the end of a water dispense, or end of a purified water fill. Thus, by the continuing passage of water in this ultrapure circuit 14 through the ion exchange module 28 one or more further times with the same water, after the initial passage of purified water described above, there can be taken one or more further resistivity measurements of the water by the in-line cell 40 after the further passages through the ion exchange module 38 to provide one or more further resistivity values $R_{2+}$. Preferably, such further resistivity measurements are taken periodically, and they can be compared with $R_1$ and/or $R_{new}$ to further determine the effectiveness of the ion exchange module 38.

For example, a comparison of the difference, such as the quantitative difference, between $R_1$ and a $R_2$ or $R_3$ or $R_4$, etc. value, can show the ability of the resin in the ion exchange module 36 to recover from the initial drop of resistivity caused by the first passage of the purified water 22 through the inlet 32, and the time and rate of the recovery of the ion exchange module 38 can be shown by the knowledge of the rate of change of $R_{2+}$, and each comparison of each $R_{2+}$ value with $R_1$.

The present invention allows the comparison to include a comparison of the quantitative difference between $R_1$, $R_{new}$ and $R_{2+}$ using one or more algorithms or other difference comparators, such as quantitative differences, especially over time, to provide their operator or user of the ultrapure circuit 14 to consider the effectiveness of the ion exchange module 38. Such algorithm(s) may also include filters for erroneous results such as electrical spikes or allow for other effects such as thermal lag of temperature sensors.

For example, FIG. 6 shows a rapid recovery of resistivity value $R_2$ after $R_{new}$, with a resistivity value $R_{10}$ being wholly or substantially similar to that of $R_1$. Thus, the user can determine that there is continuing effectiveness of the ion exchange module 38 during a time period 2600-2780 mins as expected.

FIG. 7 also shows a resistivity value $R_{10}$ returning to be similar to that of $R_1$, despite a longer time period wherein $R_{new}$ is lower than a value of 18 MΩ·cm, showing the continued effectiveness of the ion exchange module 38.

FIG. 8 shows a lower and more pronounced $R_{new}$ whose difference from R1 at 0.2 Mohm·cm is greater than the errors attributable to the line cell.

Recovery to over 18 Mohm·cm is rapid and although the ion exchange module 38 is being effective, this is a first measurable indication that the pack is starting to exhaust. The ion exchange module is likely in all but extreme cases to still be satisfactory for continuing use.

FIG. 9 shows a significantly lower and long term $R_{new}$ or $R_{min}$. The recovery of R10 to 18.1 Mohm·cm may be over an acceptable time period such that there is continuing effectiveness of the ion exchange module 38 at 9450. Using known exhaustion detection methods, the decrease to $R_{new}$ and $R_2$ etc. would not be sufficient to indicate an alarm condition to the user to replace the pack. However, using the method of the present invention, a comparison of $R_{new}$ and $R_1$ and/or $R_2$ etc. can be used to indicate to the user that it is time to replace the ion exchange module while the levels of contaminants in $R_{10}$ are still <1 ppb.

FIG. 10 shows an even further drop in resistivity for $R_{new}$ or $R_{min}$, with $R_{2-10}$ no longer being able to achieve a resistivity value above 18 Mohm·cm. Conventionally, this may have been the first point where a change of ion exchange module may have been indicated to a user, as $R_{10}$ is less than 18 Mohm·cm. However, this indication may still have been attributable by the user to 'errors in the system', depending upon quality of the resistivity and temperature sensors used, such that the user may continue to use the ion exchange module. However by this time the levels of contaminants in the water, even after recirculation ($R_{10}$), are now likely to be above 1 ppb, as shown in FIG. 4 and table 1. If higher levels of contaminants are acceptable to the user, say at a level of 2 ppb, then this may be the indicative time to the user to change the ion exchange module.

FIG. 11 shows an even lower $R_{new}$ value, as well as even lower $R_{2-10}$ values during the 13014-13194 minute period of FIG. 5. Conventionally, when $R_{10}$ is less than 17 Mohm·cm, this would be the typical time to change ion exchange module due to the lower quality of sensors being used.

Thus, a detailed examination and comparison of resistivity values at different time periods, as exampled by FIGS. 6-11, can reveal a more detailed understanding of the effectiveness of the ion exchange module 38, not only through the drop in resistivity after the introduction of a new portion of purified water 22, but the recovery of the resistivity after subsequent passages of water in the ultrapurified circuit 14. This provides a much more detailed assessment of the effectiveness of the ion exchange module 38, rather than relying on the simple viewing of the progression of resistivity over time as shown in FIG. 3.

In particular, the analysis of resistivity provides a method of determining the presence of one or more contaminant ions such as silica at a level of less than one part per billion in an ultrapure water stream, based on the length and speed of recovery of resistivity value back to a benchmark resistivity value.

The invention claimed is:

1. A method for monitoring the effectiveness of an ion exchange module in an ultrapure water purification circuit containing ultrapurified water and having a purified water inlet and a point of use outlet and a memory, the method comprising the steps of:
    (a) passing the water in the circuit through the ion exchange module a multiple of times to provide ultrapurified water;
    (b) measuring the resistivity of the ultrapurified water provided by step (a) using one or more sensors to provide an ultrapurified benchmark resistivity value $R_i$;
    (c) storing the value $R_i$ in the memory;
    (d) introducing purified water into the circuit through the inlet;
    (e) passing the water in the circuit including the purified water of step (d) through the ion exchange module;
    (f) measuring the resistivity of the water after step (e) to provide a new water resistivity value $R_{new}$; and
    (g) comparing $R_i$ and $R_{new}$ to determine the effectiveness of the ion exchange module.

2. A method as claimed in claim 1 wherein the purified water has a resistivity of >0.03 MΩ·cm (at 25° C.).

3. A method as claimed in claim 1 wherein $R_i$ is >18.0 MΩ19 cm.

4. A method as claimed in claim 1 wherein the circuit also includes a water reservoir.

5. A method as claimed in claim 1 wherein the circuit comprises <20 liters of water.

6. A method as claimed in claim 1 wherein step (d) is preceded by the outflow of water in the circuit through the point of use outlet.

7. A method as claimed in claim 1 wherein the comparison in step (g) includes a time element.

8. A method as claimed in claim 1 wherein the comparison in step (g) includes a quantitative comparison of the resistivity values.

9. A method as claimed in claim 8 wherein the comparison of step (g) further includes a comparison of the quantitative difference between $R_i$ and $R_{new}$.

10. A method as claimed in claim 9 wherein the comparison of $R_{new}$ being greater than a predetermined quantitative difference from $R_i$ determines non-effectiveness of the ion exchange module.

11. A method as claimed in claim 10 wherein a comparison of $R_i$ and $R_{new}$ being >0.2 MΩ·cm determines non-effectiveness of the ion exchange module.

12. A method as claimed in claim 1 further comprising the steps of: (h) passing the water in the circuit after step (f) through the ion exchange module one or more further times;
    (i) taking one or more resistivity measurements of the water after step (h) to provide one or more further resistivity values $R_{2+}$; and (j) comparing at least one of the $R_{2+}$ values and $R_{new}$ to further determine the effectiveness of the ion exchange module.

13. A method as claimed in claim 12 wherein the further resistivity measurements are taken either periodically, regularly or continuously.

14. A method as claimed in claim 12 wherein the further measurements are conducted over a time period to monitor resistivity of the water in the circuit over time.

15. A method as claimed in claim 12 wherein the comparison of step (j) further includes a comparison of the quantitative difference between $R_i$ and $R_{2+}$.

16. A method as claimed in claim 15 wherein the comparison of $R_{2+}$ being greater than a predetermined quantitative difference from $R_i$ determines non-effectiveness of the ion exchange module.

17. A method as claimed in claim 12 wherein the comparison of step (j) further includes a comparison of the quantitative difference between $R_i$, $R_{new}$ and $R_{2+}$.

18. A method as claimed in claim 12 wherein the comparison in step (j) includes a time element.

19. A method as claimed in claim 1 wherein the ultrapure water purification circuit is part of a water purification apparatus providing the purified water.

20. A method as claimed in claim 1 wherein the ion exchange module comprises an ion exchange cartridge.

21. A method as claimed in claim 1 wherein the ultrapure water purification circuit includes a recirculation line.

22. A method of determining the presence of one or more contaminants at a level <1 parts per billion (ppb) in an ultrapure water stream using a method as defined in claims 1.

* * * * *

UNITED STATES PATENT AND TRADEMARK OFFICE
CERTIFICATE OF CORRECTION

| | |
|---|---|
| PATENT NO. | : 9,134,264 B2 |
| APPLICATION NO. | : 13/995865 |
| DATED | : September 15, 2015 |
| INVENTOR(S) | : Paul Whitehead et al. |

Page 1 of 1

It is certified that error appears in the above-identified patent and that said Letters Patent is hereby corrected as shown below:

In The Claims

Claim 3, Col. 14, line 49, please replace "MΩ19 cm" with -- MΩ cm --

Claim 22, Col. 15, line 31, please replace "claims 1" with -- claim 1 --

Signed and Sealed this
Ninth Day of February, 2016

Michelle K. Lee
*Director of the United States Patent and Trademark Office*